United States Patent [19]

Letsinger et al.

[11] Patent Number: 5,681,943
[45] Date of Patent: Oct. 28, 1997

[54] METHOD FOR COVALENTLY LINKING ADJACENT OLIGONUCLEOTIDES

[75] Inventors: Robert Lewis Letsinger, Wilmette, Ill.; Sergei M. Gryaznov, San Mateo, Calif.

[73] Assignee: Northwestern University, Evanston, Ill.

[21] Appl. No.: 436,145

[22] Filed: May 8, 1995

Related U.S. Application Data

[63] Continuation-in-part of Ser. No. 376,688, Jan. 23, 1995, Pat. No. 5,476,930, which is a continuation of Ser. No. 46,032, Apr. 12, 1993, abandoned.

[51] Int. Cl.$^6$ .............................. C07H 1/00; C07H 21/00
[52] U.S. Cl. ...................... 536/25.33; 536/24.5; 536/25.3
[58] Field of Search ........................... 536/25.3, 25.33, 536/24.5

[56] References Cited

FOREIGN PATENT DOCUMENTS

WO07582  7/1990  WIPO.

OTHER PUBLICATIONS

Gryaznov et al.: "Template Controlled Coupling and Recombination of Oligonucleotide Blocks Containing thiophosphoryl Gropus." *Nucleic Acids Research* 21: 1403–1408 (1993) month not available.

Ashley and Kushlan, "Chemical synthesis of oligoeoxynucleotide dumbbells" *Biochemistry* 30:2927–2933 (1991). month not available.

Bischofberger and Wagner, "Antisense approaches to antiviral agents" *Virology* 3:57–66 (1992). month not available.

Chu and Orgel, "Ligation of oligonucleotides to nucleic acids or proteins via disulfide bonds" *Nucleic Acids Res.* 16:3671–3691 (1988) month not available.

Crooke & Lebleu, Ed. *Antisense Research and Application.* CRC Press, Boca Raton, Florida month not available.

Danheiser, "Advances in DNA probe–based assays lead to second–generation products" *Genetic Eng. News*, pp. 6–7 (1994) month not available.

Gibbs, "DNA amplification by the polymerase chain reaction" *Analytical Chem.* 62:1202–1214 (1990) month not available.

Goodwin and Lynn, "Template–directed synthesis: use of a reversible reaction" *J.Am.Chem.Soc.* 114:9197–9198 (1992) month not available.

Gryaznov et al., "Enhancement of selectivity in recognition of nucleic acids via chemical autoligation" *Nucleic Acids Res.* 22:2366–2369 (1994) month not available.

Gryaznov and Letsinger, "Chemical ligation of oligonucleotides in the presence and absence of a template" *J. Am. Chem. Soc.* 115:3808–3809 (1993a) month not available.

Gryaznov and Letsinger, *Nucleic Acids Res.*, 114:9197–9198 (1993b) month not available.

Gryaznov and Letsinger, "Anchor for one step release of 3'-Aminooligonucleotides from a solid support" *Tetrahedron Lett.*, 34:1261–1264 (1993c) month not available.

Gryaznov and Letsinger, "Synthesis and properties of oligonucleotides containing aminodeoxythymidine units" *Nucleic Acids Res.* vol. 20, No. 13, 3403–3409 month not available.

Helen and Toulme, "Specific regulation of gene expression by antisense, sense and antigen nucleic acids" *Biochem. Biophys. Acta*, pp. 99–125 (1990) month not available.

Jablonski et al., "Preparation of oligodeoxynucleotide–alkaline phosphatase conjugates and their use as hybridization probes" *Nucleic Acids Res.* 14:6115–6128 (1986) month not available.

Kool, "Molecular recognition by circular oligonucleotides: increasing the selectivity of DNA binding" *J.Am.Chem.Soc.* 113:6265–6266 (1991) month not available.

Lau et al., "Significance of serum hepatitis C virus RNA levels in chronic hepatitis C" *Lancet* 341:1501–1504 (1993) month not available.

Letsinger and Wu, "Control of excimer emission and photochemistry of stilbene units by oligonucleotide hybridization" *Amer. Chem. Soc.*, 116:811–812 (1994) month not available.

Lewis, *Adv. Photchem* 13:165–235 (1986) month not available.

Luebke and Dervan, "Nonenzymatic sequence–specific ligation of double–helical DNA" *J.Am.Chem.Soc.* 113:7447–7448 (1991) month not available.

Luebke and Dervan, "Nonenzymatic ligation of double–helical DNA by alternate–brand triple helix formation" *Nucleic Acids Res.* 20:3005–3009 (1992) month not available.

Maniatis, et al., *Molecular Cloning,* Cold Springs Harbor Lab., pp. 382–389 (1982) month not available.

*NAMA Proceedings,* International Confernece on Nucleic Acid Medical Applications, Cancun, Mexico, Jan. 26–30, 1993, pp. 59–63 month not available.

Naylor and Gilham, "Studies on some interactions and reactions of oligonucleotides in aqueous solution" *Biochemistry* 5:2722–2728 (1966) month not available.

Peters et al., "Picosecond dynamics of trans–stilbene photo–dimerization" *J. Phys. Chem.*, 97:5482–5485 (1993) month not available.

(List continued on next page.)

Primary Examiner—Gary L. Kunz
Attorney, Agent, or Firm—Kohn & Associates

[57] ABSTRACT

A method for increasing oligonucleotide selectivity comprising reversibly binding two oligonucleotides at adjacent positions to the bases on a complementary template and then spontaneously and irreversibly covalently joining said oligomers via two reactive groups brought into proximity of each other by the binding of the oligonucleotides, in the absence of added reagent or enzyme. By using a shorter, lower affinity, highly selective first oligonucleotide complementary which binds to the site of a point mutation combined, with a longer, high affinity, less selective second oligonucleotide, this method provides an effective way to identify the presence of absence of a point mutation.

23 Claims, 3 Drawing Sheets

OTHER PUBLICATIONS

Prakash and Kool, "Structural effects in the recognition of DNA by circular oligonucleotides" *J.Am.Chem.Soc.* 114:3523–3527 (1992) month not available.

Purmal et al., "A new affinity reagent for the site-specific, covalent attachment of DNA to active–site . . . " *Nucleic Acids Res.* 20:3713–3719 (1992) month not available.

Roberts, "In situ hybridization: nowhere to hide for nucleotides" *J. NIH Res.*, 2:82–85 (1990) month not available.

Salunkhe et al., "Control of folding and binding of oligonucleotides by use of a nonnucleotide linker" *J. Am. Chem. Soc.*, 114:8768–8772 (1992) month not available.

Shabarova, "Chemical development in the design of oligonucleotide probes for binding to DNA and RNA" *Biochimie* 70:1323–1334, (1988) month not available.

Sokolova et al., "Chemical reactions with DNA duplexes: cyanogen bromide as an effective oligoeoxyribonucleotide . . . " *FEBS Letters* 232:153–155 (1988) month not available.

Twomey and Krawetz, "Parameters affecting hybridization of nucleic acids blotted onto nylon or nitrocellulose membranes" *Biotechniques* 8(5)478–482 (1990) month not available.

Uhlman and Peyman, "Antisense oligonucleotides: a new therapeutic principle" *Chem.Rev.* 90:544–584 (1990) month not available.

Urea et al., "A comparison of non–radioisotopic hybridization assay methods using fluorescent, chemiluminescent . . . " *Nucleic Acids Res.* 16:4937–4956 (1988) month not available.

Urea et al., "Application of a rapid non–radioisotopic nucleic acid analysis system to the detection of sexually transmitted . . . " *Clinical Chemistry,* 35:1571–1575 (1989) month not available.

van Ness and Chen, "The use of oligodeoxynucleotide probes in chaotrope–based hybridization solutions" *Nucleic Acids Res.* 19:5143–5151 (1991) month not available.

Vries et al., "A dot–blot screening procedurea for mutated ras oncogenes using synthetic oligodeoxynucleotides" *Gene* 50:313–320 (1986) month not available.

Woolf et al., "Specificity of antisense oligonucleotides in vivo" *Proc. Natl. Aced. Sci.* 88:7305–7309 (1992) month not available.

Zhang et al., "Single–base nutational analysis of cancer and genetic diseases using membrane bound modified oligonucleotides" *Nucleic Acids Research,* vol. 19, No. 14, pp. 3929–3933 (1991) month not available.

SYSTEM 1

TEMPLATE: 3'GGXGATAAACAGTYGG  4a, X=A, Y=A
4b, X=T, Y=A
4c, X=A, Y=T

METHOD FOR COVALENTLY LINKING ADJACENT OLIGONUCLEOTIDES

This application is a continuation-in-part of U.S. Ser. No. 08/376,688, filed Jan. 23, 1995, now U.S. Pat. No. 5,476,930, which is a continuation of U.S. Ser. No. 08/046,032, filed Apr. 12, 1993, now abandoned.

GRANT REFERENCE

The research carried out in connection with this invention was supported in part by grants from the National Cancer Institute and the National Institute of Allergy and Infectious Diseases (Grant UOI AI24846) and the National Institute of General Medical Sciences (Grant 10265). The U.S. Government has certain rights in this invention.

TECHNICAL FIELD

The present invention relates to a method of enhancing selectivity in recognition of nucleic acids and more specifically relates to methods having use as diagnostic methods for diseases or disorders involving mutations in nucleic acid sequences as well as therapeutic applications of oligonucleotides.

BACKGROUND OF THE INVENTION

Oligonucleotides in Diagnostics

Oligonucleotide probes currently serve as useful tools in the diagnosis of genetic, bacterial, and viral diseases. In view of the rapid developments in molecular and cell biology, the research activity and the new leads in probe technology generated in industrial laboratories (Danheiser, 1994), and the rapidly expanding knowledge of the human genome, one can expect a growing list of new medical applications in the future.

Figure 1:
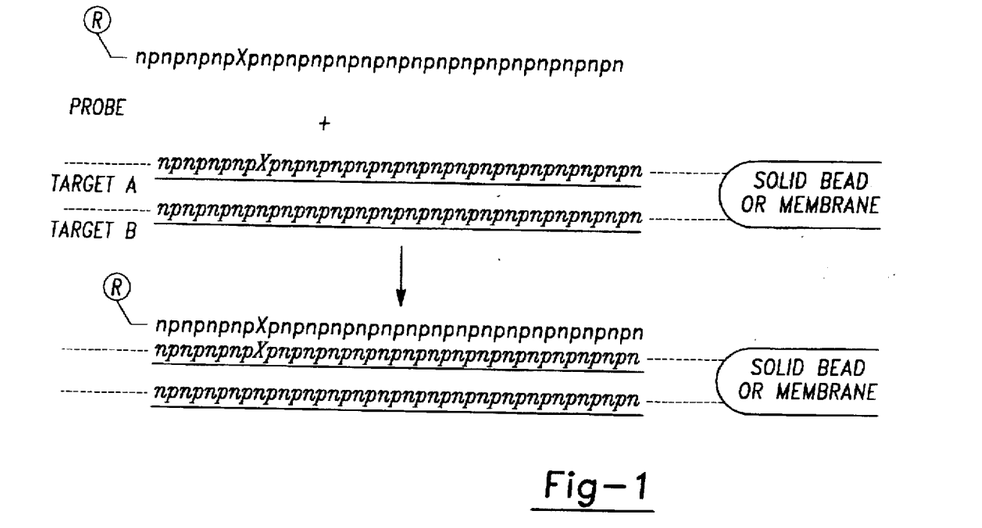
FIG. 1 is a schematic representation of typical prior art hybridization probe methodology for screening for a point mutation wherein R represents a reporter group (e.g. a radioactive atom or a group than can give an observable signal; the np's represent nucleotide units in a given polynucleotide sequence of an immobilized polynucleotide, Xp represents a point mutation, i.e., a nucleotide unit differing from that in the corresponding position in the sequence for the wild type polynucleotide, the np's represent nucleotide units in a probe complementary to the segment containing np's in a target probe; Xp represents a nucleotide complementary to Xp, — represents oligonucleotide segments in the target.

The basic idea underlying the probe technology is represented in FIG. 1. The polydeoxyribo- or polyribonucleotide target strands are immobilized on a solid surface, membrane, or bead. A probe oligonucleotide bearing a marker for identification is then added under stringent conditions for hybridization, so that the probe binds non-covalently and selectively to any region of the target in which the sequence is complementary to that in the probe. Residual probe oligonucleotide is then washed away from the immobilized target oligonucleotide, and the presence of any bound probe is observed by means of an attached reporter group. Common reporter groups include radioactive atoms (phosphorous, sulfur, carbon, or tritium), fluorescent or chemiluminescent groups, and enzymes that generate colored or fluorescent products. Some specific experimental procedures are given. (Jablonski et al, 1986; Urdea et al., 1988; Twomey and Krawetz, 1990; Lau et al, 1993; Maniatis et al., 1982). In practice, the techniques may be elaborated in a variety of ways, including use of chaotropes (van Ness and Chen, 1991), sandwich hybridization complexes (Urdea et al., 1989), and in situ hybridization (Roberts, 1990), and sensitivity can be increased by target amplification by the polymerase chain reaction (Gibbs, 1990) or by signal amplification (Urdea et al., 1989).

A limitation in the sensitivity of the probe technology arises from non-specific binding of the oligonucleotide probes to immobilized DNA or RNA targets. As noted by Roberts (1990): "Despite the many advances in the technique of in situ hybridization, the problem of nonspecific labeling, which creates false positive signals, plagues many researchers. In addition to binding to complementary nucleotide sequences as they are supposed to, probes may also adhere to non-matching sequences, to proteins, and even to microscope slides." This problem is particularly acute when a single nucleotide mismatch in the probe and target sequence occurs.

One needs relatively long oligonucleotide sequences to achieve good affinity in binding to the target. Generally probes in the 20 to 40 nucleotide range are used. Also, for unique recognition of genes in human DNA, it is estimated on a statistical basis that a minimum of 17 nucleotide units must be present in the probe. On the other hand, although binding affinity increases with increasing size of the probe, selectivity with respect to mismatches decreases. A mismatch in a long oligomer is less destablizing than a mismatch in a shorter oligomer.

Oligonucleotides as Therapeutic Agents

Synthetic oligonucleotides are being extensively used as sequence specific antisense agents (Helene 1990, Uhlman 1990, Crooke 1993), as well as probes for hybridization based detection assays of nucleic acids (Lowe 1986; Urdea 1988). Antisense oligonucleotides have demonstrated potential as new types of therapeutic agents for treating such diseases and disorders as viral diseases, cancer, genetic disorders, as well as other diseases and disorders (Bischofberger and Wagner, 1992). A problem encountered with the approach of utilizing antisense oligonucleotides as therapeutic agents concerns the selectivity of the agents in vivo: the antisense oligonucleotides can form complexes with targets that are not fully complementary. Relatively long oligomers (e.g. ~20-mers) are needed to provide a unique sequence and a high binding affinity in targeting human genetic segments; however, the longer oligomers are not highly selective as antisense agents (Woolf, 1992). Short oligomers (e.g. 7–12 mers), which bind with low affinity, are much more effective in discriminating between complementary strands and targets containing one or more mismatches. In view of the low concentrations of intracellular polynucleotide targets and the low concentrations of therapeutic oligonucleotides that can be introduced into cells, it is recognized that there is a need for oligonucleotides with high binding affinities. The binding affinity is related to the length of the oligomers, preferably 20-mers and longer are desirable. But, in the case of long oligomers, a mismatch in base pairing is less destabilizing then in the case of a short oligomer. Hence, the desired destabilizing effect is lessened by the use of longer oligomers, while the selectivity is increased.

Experts have noted that "high sequence specificity" and "high affinity" are contradictory demands for an antisense oligonucleotide (NAMA Inter. Conference, 1993, pp 59–64), and have further concluded that it is probably not possible to stimulate cleavage of a specific RNA (and thereby inactivate it) by use of an antisense oligonucleotide without at least partial destruction of many non-targeted RNA's (Woolf, 1992). Hence, experts in the field, based on conducted research, have concluded that the conflicting requirements of high specificity and high affinity are major hurdles to overcome.

Chemical Ligation

Several chemical methods have been reported for irreversibly covalently linking oligonucleotide blocks in aqueous media (Naylor and Gilham, 1966; Sokolova et al, 1988; Shabarova, 1988; Chu, 1988; Kool, 1991; Ashley and Kushlan, 1991; Luebke and Dervin, 1991; Luebke and Dervan, 1992; Prakash and Kool, 1992; Purmal et al, 1992; Gryaznov and Letsinger, 1993b; Goodwin and Lynn, 1992). All of these methods require an additional chemical agent to yield a stable ligated product. Depending on the approach, the added reagent may be an "activating agent" such as a water soluble carbodiimide or cyanoimidazole or it may be an oxidizing agent such as $K_3Fe(CN)_6$ (Gryaznov and Letsinger, 1993b) or a reducing agent such as sodium cyanoborohydride (Goodwin and Lynn, 1992). In any case, the need for the third reagent precludes chemical ligation in vivo since such compounds are toxic, react with water, and could not be introduced into living systems in sufficient amounts to bring about the desired coupling reaction.

The present invention provides a novel method designed to capitalize on the positive features of both the longer and the shorter oligomeric reagents to enhance selectivity in recognition of polynucleotide sequences. It is based on spontaneous and irreversible in situ chemical ligation (linking) of relatively short oligomer fragments equipped with electrophilic bromoacetamido and nucleophilic phosphorothioate groups at their termini. Selective recognition is achieved without need for an additional condensing or stabilizing reagent. It therefore opens the door for in situ chemical ligation in living systems. Hence, the present invention could solve the problem of the conflict of achieving both high affinity and high selectivity in therapeutic applications as well as in diagnostic and chemical amplification systems.

Goodwin and Lynn (1992) have developed another system designed to enhance selectivity. Their approach utilized condensation of an amine with an aldehyde and was based on achieving "equilibrium between the transiently coupled and uncoupled substrates." This chemistry made necessary addition of another chemical agent (sodium cyanoborohydride) to reduce the reversible intermediate. As a consequence, their approach would not be suitable for use in living cells.

SUMMARY OF THE INVENTION AND ADVANTAGES

In accordance with the present invention, there is provided a method of increasing oligonucleotide selectivity in recognition of nucleic acids, the method including the steps of disposing in aqueous solution a first oligomer wherein the first oligomer has high selectivity for a target polynucleotide and a second oligomer has high affinity for the target polynucleotide. The oligonucleotides including first and second reactive groups capable of spontaneously and irreversibly forming covalent bonds between the oligomers when the oligonucleotides are aligned on a target polynucleotide.

Additionally, in accordance with the present invention, there is provided a method for hybridizing nucleic acids which includes the steps of reversibly binding a first oligomer to a target oligo- or polynucleotide including base units complementary to base units of the oligonucleotide, reversibly binding a second oligomer to the target oligo- or polynucleotide including base units complementary to base units of the oligonucleotide adjacent to the first oligomer, and wherein one of the oligomers includes a nucleotide having a first reactive group proximate to a nucleotide of the other oligomer which includes a second reactive group capable of spontaneously forming a covalent bond with the first reactive group.

The method further includes the steps of irreversibly covalently joining the oligomers together through the first and the second reactive groups having been brought in proximity to each other upon binding of the oligonucleotides on the target polynucleotide in the absence of added reagent or enzyme, dissociating the joined first and second oligomers from the target polynucleotide, and removing the target polynucleotide.

An important feature of the chemistry utilized in the present invention is that covalent linkage of the two probes depends on a polynucleotide template and no additional activating agents or enzymes are needed.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

In accordance with the present invention there is provided a method of increasing oligonucleotide selectivity in recognition of nucleic acids, generally by the steps of disposing a first highly selective oligomer and a second highly affinitive oligomer in aqueous solution and then covalently binding the oligomers together.

By highly selective, it is meant that the degree to which the oligomer binds to its fully complementary strand is much greater than the degree to which the oligomer will bind to a non-complementary strand. A highly selective oligomer binds with high preference to the exact complementary sequence on a target strand as compared to a sequence which has one or more mismatched bases.

By high affinity, it is meant that the dissociation constant for a complex formed from a probe and a target polynucleotide is very small. In other words, nucleotides sequences of the oligomer and the target polynucleotide are very closely related. That is, the oligomer and the target share a high degree of complementary base pair homology. Therefore, the high degree of complementarity provides for bonding forces which draw the complementary strands together and tends to keep the strands combined.

The present invention is based on the ligation chemistry developed by Gryaznov and Letsinger and demonstration that ligation of two oligomers by this chemistry shows a degree of selectivity with respect to proper base pairing that is characteristic for the selectivity exhibited by a short probe involved in the coupling (Gryaznov et al. 1994). This method exploits the fact that the coupling reaction described herein is very slow in very dilute aqueous solutions but is fast in the presence of a template polynucleotide. The reaction is accelerated in the presence of a target polynucleotide that possesses the sequence section complementary to the probe oligomers.

The ligation chemistry employs two short oligomers (for example, 8 to 20-mers) which will spontaneously link together covalently after binding at adjacent positions on a target polynucleotide. With this system, one will approach the binding affinity and recognition properties of a longer oligomer probe such as between 16 to 40-mer, but retain the dependency and base pairing characteristics of the shorter probes (8 to 20-mer).

Examples of such pairs or reactive groups are ester+ hydrazide, RC(O) S⁻+haloalkyl and RCH₂S⁻+α-haloacyl group, such as a bromacetylamino group and a thiophosphoryl group, which form a thiophosphorylacetylamino bridge efficiently, selectively, and irreversibly in dilute aqueous media. As demonstrated below, the products are stable in water and hybridize well with complementary polynucleotides.

At low oligomer concentrations, such as less than 1 μM, and in absence of a complementary template, the reactions are very slow but can be carried out to high conversion within a few days by freezing the solution. The freezing techniques are described in detail below. Coupling is quite fast (greater than 90% conversion in 20 minutes) when carried out in solution in the presence of a complementary oligonucleotide that serves as a template, as shown below in the Example section.

The present invention combines the advantages of short probes with respect to selectivity with the advantages of long probes with respect to affinity by utilizing two oligonucleotide probes that spontaneously link covalently, irreversibly, rapidly, and efficiently when aligned on an polynucleotide target. The method of the present invention can be applied both in diagnostic applications and in "antisense" therapeutic applications.

Diagnostic Applications

The chemistry of the present invention is especially suitable for detection of point mutations. Two methods for utilizing the chemistry of the present invention in diagnostic applications are described below. One method (Method I) is adapted to the techniques for conventional probe work in which the target polynucleotide is immobilized. The second method (Method II) is based on a novel approach, made possible by the chemistry of the present invention, which involves transient immobilization of the target oligonucleotide.

Figure 2:
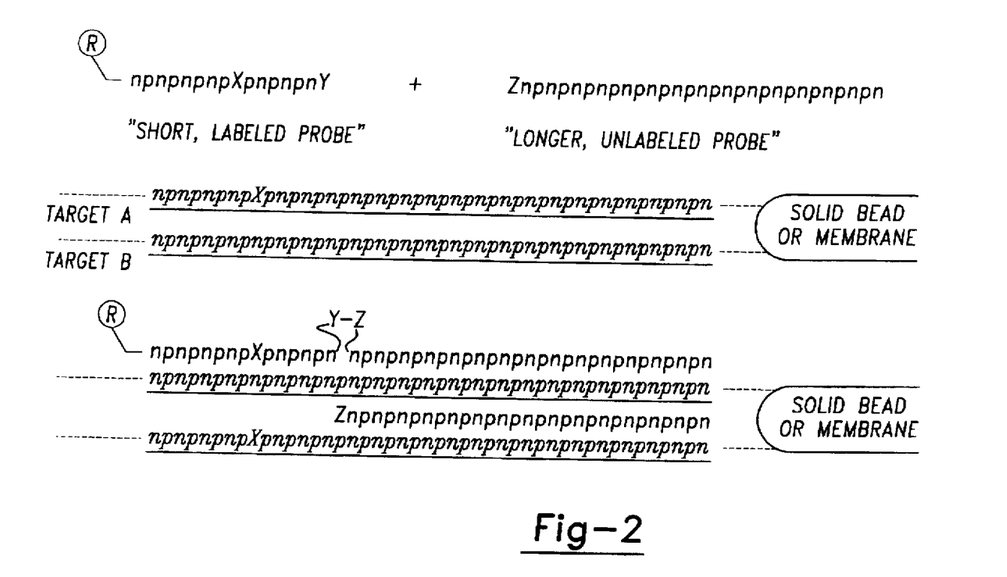
FIG. 2 is a schematic representation of the hybridization technology of the present invention utilizing methodology I using a short, labelled probe and a longer unlabelled probe that undergo autoligation on an immobilized, matching polynucleotide (Target A), Y and Z represent functional groups (on the probes) which covalently and irreversibly join when the probes are aligned on the target polynucleotide, other notation is the same as in FIG. 1.

Method I: The concept is generally indicated in FIG. 2. The problem is to recognize a small amount of polynucleotide A in the presence, or absence, of polynucleotide B. In the region to be screened, A and B differ only in one nucleotide, X, or a few nucleotides. Two probe oligonucleotides are used. One is a short oligonucleotide (e.g. 7–20 nucleotides) containing a marker group (R) for detection, a nucleoside (X') complementary to X in the target (preferably positioned near the center of the probe) and a coupling group (e.g., bromoacetylamino or phosphorothioate) at a terminus. The other probe is a longer oligonucleotide (e.g. 10–40 nucleotides) with an appropriate coupling group (bromoacetylamino when a phosphorothioate group is used on the other probe or a phosphorothioate group when a bromoacetyl group is used on the other probe) at the end adjacent to the other probe when aligned on the target. On hybridization and coupling on the target polynucleotide (A) an extended probe is generated which binds cooperatively on the target. Excess unligated probes are then washed away under stringent conditions for hybridization of the ligated probe (all unligated, labeled probe must be removed; it is not necessary to remove all of the unlabeled probe), and the presence of the ligated probe is detected via the marker group (via radioactivity, fluorescence, chemiluminescence, enzyme generated signals, etc.).

Figure 3:
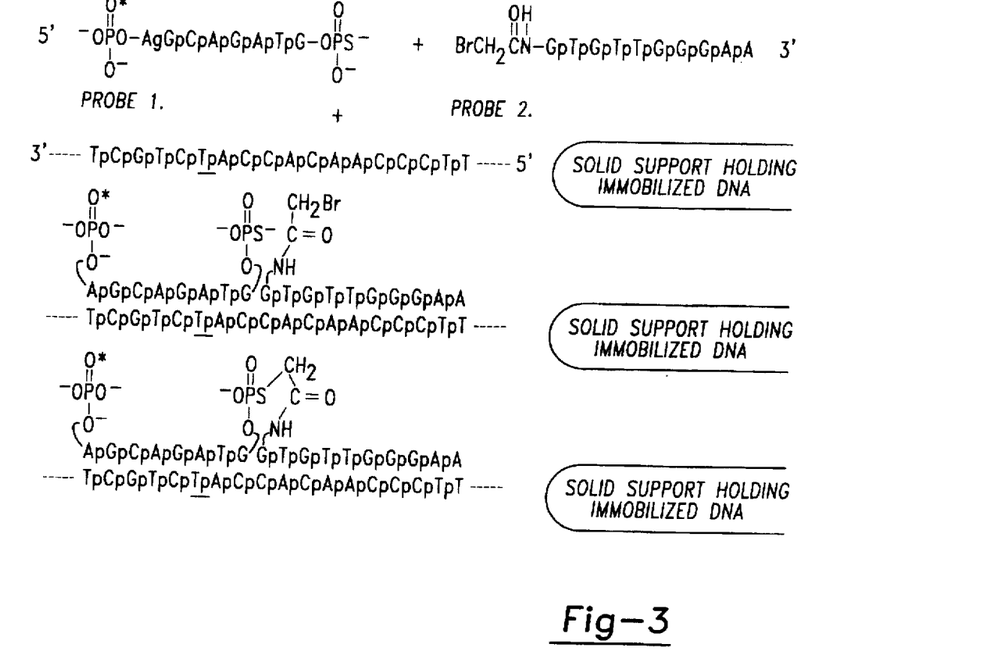
FIG. 3 is a schematic representation of oligonucleotides of the present invention for irreversibly coupling two probes (SEQ ID NO:1 and SEQ ID NO:2) in order to detect a point mutation utilizing a two-probe-bridging technique for screening immobilized DNA samples for a ras mutant containing a single point mutation (replacement of C by T at the position indicated by underlining.

The chemistry of this new approach is indicated more specifically in FIG. 3, which depicts how the method could be used to screen for a point mutation where T replaces C in a wild type genome.

Formulas for the mutant and wild type are shown below. The nucleotide at the mutation site is underlined.

Mutant (SEQ ID NO:3)

3' ... TpCpGpTpCpTpApCpCpApCpApApApCpCpCpTpT ...

Wild Type (SEQ ID NO:4)

3' ... TpCpGpTpCpCpApCpCpApCpApApApCpCpCpTpT ...

The structures of the probes for the assay and of the hybridized, bridged oligonucleotide formed after ligation are shown in FIG. 3. In this case, a modification of the dot-blot procedure of Verlaan-deVries et al. (1986) could be used for the analysis.

In a variation of this method, both of the probe oligonucleotides could be labelled or carry reporter groups, the reporter groups on each would differ so that the signals could be read independently. For example, one reporter group might be fluorescent, colored, or chemiluminescent compound and the other label could be a radioactive marker. Positive identification of a target polynucleotide could then be obtained when signals from both reporter groups are obtained after washing the immobilized target under stringent conditions for hybridization of the ligated oligonucleotide probes. In this case, it could prove advantageous to use oligonucleotide probes of about equal sizes. The method could also be extended to a three or more probe system in which two or more independent reporter groups are employed.

Method II: The "autoligation" chemistry opens the way for a new method of analysis that can be useful in screening samples for multiple point mutations. Some diseases, such as cystic fibrosis, can be caused by any one of several mutations in a gene. A convenient way to rapidly screen a sample for all the relevant mutations can, therefore, facilitate the genetic analysis. The reverse dot blot procedure of Y. Zhang et al., (1991), provides a means for such rapid screening. In this procedure, the probe oligonucleotide is bound to a surface and the target polynucleotide bearing a reporter or marker group is captured from solution as a hybridization product.

Method II is based on the reverse dot blot procedure. It differs in that both the target polynucleotide, which in this case has no reporter group, and a probe oligonucleotide, which does bear a reporter group, are captured transiently by an immobilized probe oligonucleotide. The new method is hereinafter termed "transient target hybridization analysis" since the method depends on the formation of a hybrid from the target polynucleotide and two (or more) probes, one of which is immobilized on a solid support, as previously described, and another carries a marker group that can elicit a signal for detection.

Figure 4:
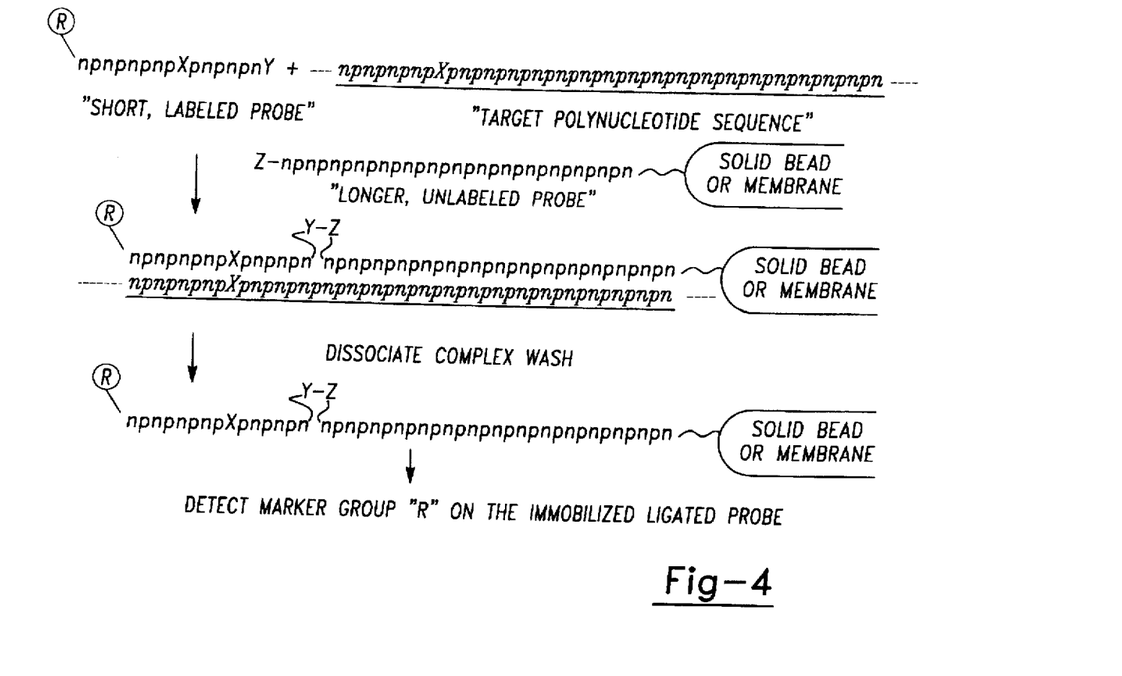
FIG. 4 is a schematic representation of the hybridization technology of the present invention for transient target hybridization analysis wherein the notations have the same significance as in FIGS. 1 and 2.

Following hybridization and autoligation of the two probes, the hybrid complex is dissociated and the target oligonucleotide is removed from the region of the support and the immobilized ligated probes before the detection measurement. Removal of the target polynucleotide from the system prior to detection of the marker group (i.e. measurement of radioactivity, fluorescence, chemiluminescence, or ultraviolet or visible spectrum) is novel. The removal of the target polynucleotide minimizes background signals arising from adventitious, non-selective binding of the high molecular weight target polynucleotide to the solid support, as described above, in conventional diagnostic procedures. The concept for this method is illustrated in FIG. 4.

In this approach, the longer, unlabelled probe is immobilized at a terminal position on a solid bead, membrane, or surface. The oligonucleotide can be covalently anchored at the 5'-position to the support via an amide bond formed from an amino linker on the oligonucleotide and a carboxy group on the membrane by the method of Y. Zhang et al., (1991), or through the 3' position by an analogous coupling utilizing an oligonucleotide with a 3'-amino group, prepared as described by Gryaznov and Letsinger, (1992). Hybridization can then be carried out with a solution containing both the "short, labelled probe" and the target oligonucleotide.

Alternatively, the target polynucleotide can be hybridized first, under stringent conditions for that binding; the unbound target polynucleotide can then be washed away; and hybridization can be carried out at a lower temperature under stringent conditions for binding the "short, labelled probe" to the target. Following autoligation of the two probes aligned on the target polynucleotide, the membrane (or other form of support) is washed again to remove excess labelled probe. The signal from the reporter group can then be read (e.g. radioactivity on the membrane determined, or chemiluminescence measured, etc.) Preferably, however, the hybridization complex is dissociated at this stage, e.g., thermally or by addition of alkali, and the liberated target polynucleotide and any "short, labelled probe oligonucleotide" that had been bound to it at any other site are washed away before the reporter signal is read.

In this example, the screening is designed for a single mutation. To screen simultaneously for many point mutations, an array of immobilized "long, unlabelled" probes could be used. The preparation of such arrays of probes on a membrane and analysis can, in principle, follow the procedures used by Y. Zhang et al., (1991), in the reverse dot blot method, with the modification indicated in discussion of Method II. The array consists of discrete spots on the membrane, each spot containing a unique probe covalently attached to the membrane. Hybridization is then carried out as in screening for a single point mutation (see FIG. 4) except a mixture of "short, labelled oligonucleotide probes" is used rather than a single labelled probe. Each probe has a unique sequence complementary to one of the potential point mutations in the target polynucleotide. Also, the sequence of each labelled probe corresponds to an extension of the sequence of one of the immobilize probes, so that, when the relevant mutation in the target is present, the oligomers will align on the target polynucleotide and undergo autoligation. The autoligation immobilizes the signal generating group at the spot of the immobilized probe. The analysis, therefore, generates a signal at each spot containing immobilized probes with sequences complementary to the sequence at a mutation site.

These methods, according to the present invention, have been illustrated for the case of two probe oligonucleotides. The methods can be extended to readily include autoligation involving three or more oligonucleotide probes. For example, for three probes, the following oligomers could be used. Also, the marker group R has been illustrated for:

R

Y=—OP(O)(O⁻)S⁻ and Z=BrCH₂C(O)NH— or

Y-BrCH₂C(O)NH— and Z=–OP(O)(O⁻)S⁻ the case where it is located at the 5' terminal position of a probe oligonucleotide. It could also be attached at any other position in the oligonucleotide that does not seriously compromise hybridization with the target, for example, at a nucleoside base ring, at a sugar position, or at the phosphate group. The R group could also be a substituent or an oligonucleotide segment that binds selectively to a fragment carrying a reporter group.

These methods for analysis of genetic material for mutations (Methods I and II) are made possible by several findings of the applicants (Gryaznov and Letsinger, 1993a; Gryaznov et al., 1994). (1) Two oligonucleotides, in which one is terminated by a phosphorothioate group and the other by a bromoacetylamino group, spontaneously couple rapidly and efficiently, with formation of an internucleoside phosphorylthioacetylamino link (—OP(O)(O)(O⁻)SCH₂C(O)NH—), when bound contiguously on a matching oligonucleotide template. (2) The bridged oligomer that is formed binds with high affinity (approaching that of a corresponding oligonucleotide containing only phosphodiester links). The two oligonucleotide segments separated by the non-nucleotide bridge in the ligated product therefore act cooperatively in the hybridization reaction. (3) At the low oligomer concentrations employed in the template driven ligation ($10^{-6}$M and less), ligation in the absence of a template oligonucleotide segment is extremely slow. (4) At appropriate temperatures (above the Tm for a mismatched probe and below the Tm for a matched probe) the rate of ligation on the template is highly dependent on the sequence of the template; a single mismatch leads to a great reduction in the rate of coupling.

Medical Applications. Oligonucleotides which have been modified to enhance stability and uptake in cells serve as effective inhibitors of synthesis of selected proteins in cells as is well known to those skilled in the art. As such they are useful tools for studies in biology. These oligonucleotides have also been found to be effective therapeutic agents in prolonging life in mice with tumors. Clinical studies on the therapeutic effects of "antisense" oligonucleotides on humans are now in progress. The modified oligonucleotides therefore have potential as therapeutic agents in treating diseases. Much work has been done with methyl phosphonate and internucleoside phosphorothioate analogues. Several other modifications, including phosphoramidate derivatives, and oligomers with modifications at the base rings and sugar moieties may also be used.

The same features of the present invention that make the chemistry attractive for diagnostic applications also make it attractive for medical applications. These are the speed and efficiency of the coupling reaction, the high dependence of the reaction on presence of a complementary template polynucleotide, the stability of the covalent link that is formed in the ligation reaction, the absence of a requirement of presence of added reagents (e.g. condensing agents, reducing agents, or oxidizing agents), the cooperativity of the two ligated oligonucleotide fragments in binding to a complementary polynucleotide, and the enhancement in selectivity in recognition of oligonucleotide sequences association with use of two or more short oligonucleotide probes as compared with a single long probe.

The procedures for using the oligonucleotides of the present invention in antisense work can be the same as employed in conventional applications of antisense oligonucleotide. The only difference is that in the present invention two or more oligomers are employed in place of one, and that the oligomers contain reactive terminal functional groups (e.g. 3'phosphorothioate at the terminal position of one oligomer and 5'bromoacetylamino at the terminal position of the other oligomer, or vice versa) that undergo spontaneous coupling when the oligomers align of the target polynucleotide in the cell, thereby affording an extended oligomer comparable to the single oligomer employed in a conventional system. In contrast to the diagnostics case, it is desirable here that each oligomer be about the same length. For example, in place of a twenty-mer conventional antisense oligonucleotide, one would use two ten-mers, each containing a terminal group to permit autoligation. Similarly, one could use three eight-mers, with appropriate terminal groups for coupling, in place of one twenty-fourmer. The oligomers used in this work can have the same modifications in the backbone, sugar, and base ring used in the conventional therapeutic and biological studies.

EXAMPLES

Example 1

For example, the present invention could be utilized in a diagnostic system as follows. The method of the present invention can be used as a diagnostic tool for detecting diseases or conditions which are caused by mutations in nucleic acid sequences such as sickle cell anemia, hepatitis C, viral infection, and cystic fibrosis.

Figure 5:
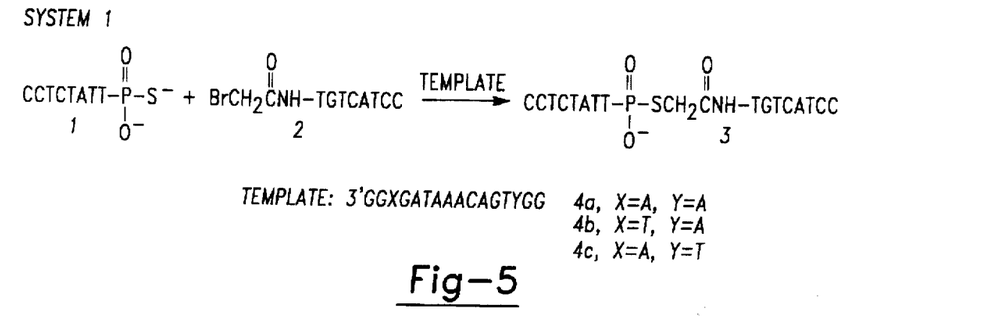
FIG. 5 is a schematic representation of the construction of oligonucleotides according to the present invention.
Figure 6A:
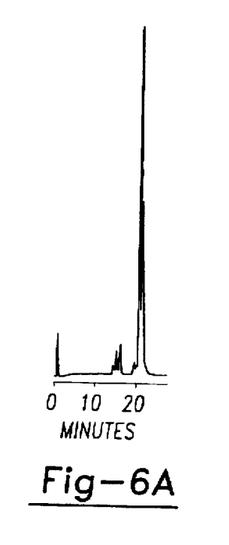
FIG. 6 is an IE HPLC of products from System I (1+2+ template 4a, 4b, or 4c) in buffer I, five minute reaction time: A, with 4a at 0° C.; B, with 4a at 30° C.; C, with 4b at 0° C.; D, with 4b at 30° C., E, with 4c at 30° C.; the peaks and assignments for A and B are, respectively: ~15.3 and 14.5 minutes (bromoacetamido derivative 2 and its hydrolysis product formed during analysis), 16.5 minutes (phosphorothioate 1); 20.9 minutes (template 4a), 21.5 minutes (product 3), the assignments are the same for B–F except templates 4a and 4b elute at ~22.5 minutes, after the product peak; the recorder sensitivity was 0.5 for A,B and 0.1 for C–F.
Figure 6B:
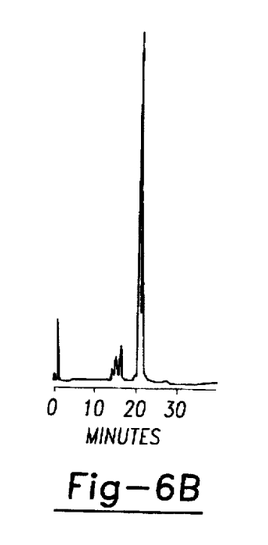
Figure 6C:
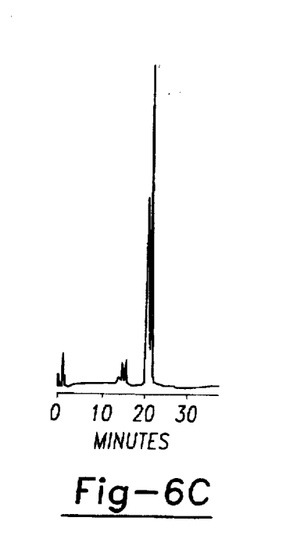
Figure 6D:
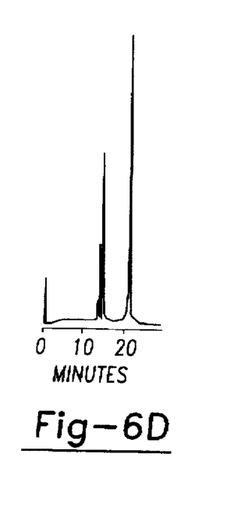
Figure 6E:
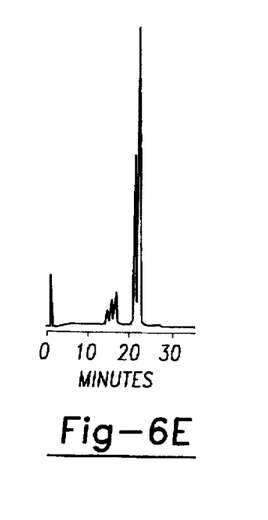
Figure 6F:
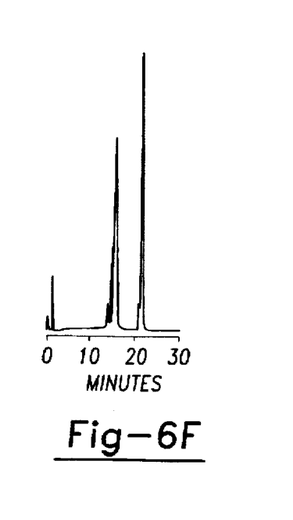

The effect of mismatches on the efficiency of coupling was demonstrated in Method I. Method I is shown in FIG. 5.

General Methods

Ion exchange high performance liquid chromatography (IE HPLC) was carried out on a Dionex Omni Pak NA 100 4×250 mm column at pH 12 (10 mM NaOH) with a 2%/min.

gradient of 1.5M NaCl in 10 mM NaOH; 1 mL/min flow rate. For analyses in System I, the gradient solution also contained MeCN (2% by volume). Reversed phase (RP) HPLC was carried out with a Hewlett Packard Hypersil ODS 5μ, 4.6×200 mm column at pH 7 in aq. 30 mM $Et_3N/HOAc$ with a 1%/min gradient of MeCN. Polyacrylamide gel electrophoresis (PAGE) was carried out with denaturing cross-linked 20% polyacrylamide gels (5% bisacrylamide); Rm values are relative to xylene cyanol. Except where otherwise noted, melting curves were obtained using solutions 0.10M in NaCl, 5 μM in each oligonucleotide, pH 7.0, by following changes in absorbance at 260 nm while ramping the temperature at a rate of 1° C./min. Oligonucleotides were prepared via automated synthesis using standard cyanoethyl phosphoramidite chemistry. They were isolated with the DMT group intact and, following detritylation (80% aq. HOAc, 15 minutes), were purified by successive RP HPLC and IE HPLC.

Preparation of CCTCTATT-P(O)(OH)S⁻

This oligomer 3'-phosphorothioate was prepared by the procedure described by Gryaznov et al. (1994) starting with "3'-Phosphate CPG" supplied by Glen Research [DMTO $(CH_2)_2SO_2(CH_2)_2O$-succinyl-lcaa CPG]. It was also prepared by the method reported by Gryaznov and Letsinger (1993a) In the former case, the DMT group was removed by DCA treatment and the support was phosphitilated with a DMT-thymidine cyanoethylphosphoramidite reagent. Following sulfurization with a 5% solution of $S_8$ in $CS_2$/pyridine (1/1 v/v) (45 minutes reaction) the oligomer (SEQ ID NO:5) was synthesized by standard protocol. After isolation by preparative HPLC, the product eluted as a clean peak on RP HPLC (16.7 minutes) and on IE HPLC, pH 12 (16.4 minutes). It formed a complex with template 4a exhibiting Tm 23° C. (0.2M NaCl); interaction with mismatched template, 4b, under the same conditions was very weak (Tm<2° C.). In support of the presence of a terminal thiophosphoryl group, oxidation of 1 $A_{260}$ unit of the oligomer in 10 μL of water with 1 μL of 1M aq. $K_3Fe(CN)_6$ (three hours at 4° C.) afforded a product eluting later on IE HPLC, as expected for oxidation of a terminal oligomer phosphorothioate to a dimeric disulfide derivative (Gryaznov and Letsinger, 1993a).

Preparation of $BrCH_2C(O)NH$-TGTCATCC

To 5 $A_{260}$ units of $NH_2$-TGTCATCC (prepared as in Gryaznov and Letsinger (SEQ ID NO:6)(1993c); elution time 16.5 minutes for IE HPLC at pH 12; Tm=32° C. with template 4a, Tm=15° C. with mismatched template 4b in 15 μL of 0.2M sodium borate buffer, pH 8.5, at room temperature was added 15 μl of 0.4M N-succinimidyl bromoacetate in MeCN. After 30 minutes, the mixture was diluted to 0.5 mL with water and desalted on a NAP-5 column. The bromacetamido derivative (3.5 $A_{260}$ units) was isolated by RP HPLC followed by lyophilization. It was homogeneous (~99% as a single peak) as judged by RP HPLC and by IE HPLC at pH 7 (30 mM $Et_3N/HOAc$, 10% MeCN with a 2%/min gradient of 1.0M NaCl, 30 mM $Et_3N/HOAc$, 10% MeCN). When analyzed by IE HPLC at pH 12, however, two peaks appeared—a major peak (~75%) at 15.4 minutes and a minor one at 14.5 minutes. Rechromatography of the product collected from the major peak again yielded the two peaks in about the same ratio. It was concluded that the minor peak is a degradation product (probably the hydroxyacetamido derivative) formed on exposing the bromoacetamido derivative to the strongly alkaline solution (pH 12) used in the chromatography. In agreement with this conclusion, the percentage of material in the faster eluting material increased to ~60% and then to >90% when the bromoacetyl derivative was exposed to a solution at pH 12 for 1 hour and for 2.7 hours, respectively, before chromatography.

Ligation Experiments

Ligations were carried out with 1 μM solutions of each oligomer in an aqueous solution (buffer I: 15 mM sodium phosphate and 0.2M NaCl, pH 7.0; or buffer II: 20 mM MES and 20 mM MgCl$_2$, pH 7.05; or buffer III: 0.1M NaCl). At the end of the designated time an aliquot was injected in the HPLC unit for IE chromatography at pH 12. This pH was selected to denature oligonucleotide complexes in the system. The structure assigned to ligation product 3 is supported by the elution time on IE HPLC (close to values for 16-mers 4a–c) and the melting curve for the complex of 3 with 4a; Tm=56° C. for 4 μM of the complex in 0.1M NaCl. Under the same conditions Tm=62° C. for a natural phosphodiester duplex with the same nucleotide sequence.

Ligation studies with CCTCTATT-OP(0)(OH)S$^-$ (1) and BrCH$_2$C(0)NH-TGTCATCC (2) were carried out in solutions 1 μM in each oligomer at pH 7.0 (15 mM sodium phosphate and 0.2M NaCl). Products were analyzed by ion exchange HPLC at pH 12. In absence of a template, no ligation was observed for reactions carried out for 45 minutes at either 0° C. or 30° C. In marked contrast, rapid ligation occurred when an appropriate template was present. HPLC profiles are shown in FIG. 6 for reactions carried out for five minutes at 0° C. or 30° C. in presence of a template (~10% excess template) that was either fully complementary or contained one mismatch. The tallest peak in each profile corresponds to the template. The ligation product is the peak eluting immediately after the template (compound 4a; SEQ ID NO:7) in FIG. 6 (A, B) and just before the template (compound 4b (SEQ ID NO:8) or 4c (SEQ ID NO:9) in FIG. 4 (C,E). Residual thioate (1) appears at 16.5 minutes and the residual bromoacetamido derivative appears as a double peak at 14.5 and 15.3 minutes (the 14.5 peak is formed during chromatography at pH 12). At 30° C., the ligation efficiency is markedly dependent on proper base pairing. From the peak areas, it is estimated that the conversion of 1 and 2 to 3 was approximately 75% when the fully matched template (4a) was present, FIG. 6 (B), but ligation amounted to less than 5% when a single mismatch occurred in a segment of the template binding to either oligomer 1, FIG. 6 (D), or to oligomer 2, FIG. 6 (F). Proper base pairing proved to be much less important at 0° C., where the binding affinity is much greater even when the template has a mismatched base. At this temperature, conversion to the ligated product amounted to 85%, 78%, and 74% for mixtures containing 4a (FIG. 6A, matched template) and 4b, and 4c (FIG. 6 (C,E), mismatched templates), respectively. When the reaction was carried out with a slight excess of the bromoacetamido derivative, 2, the yield of ligated product based on consumption of the limiting reagent, 1, was 94% and 97% for 4 minutes ligation on matching template 4a at 0° C. and at 22° C., respectively.

Throughout this application various publications are referenced by citation or number. Full citations for the publications referenced by number are listed below. The disclosures of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

REFERENCES CITED

Ashley and Kushlan (1991) Biochemistry 30:2927–2933.
Bischofberger and Wagner (1992) Virology 3:57–66
Chu and Orgel (1988) Nucleic Acids Res. 16:3671–3691.
Crooke & Lebleu, Ed. (1993) Antisense Research and Application (CRC Press, Boca Raton, Fla.)
Danheiser (1994) Genetic Eng. News, pp. 6–7
Gibbs (1990) Analytical Chem. 62:1202–1214
Goodwin and Lynn (1992) J. Am. Chem. Soc. 114:9197–9198.
Gryaznov et al. (1994) Nucleic Acids Res. 22:2366–2369
Gryaznov and Letsinger (1993a) J. Am. Chem. Soc., 115:3808–3809.
Gryaznov and Letsinger (1993b) Nucleic Acids Res. 114:9197–9198.
Gryaznov and Letsinger (1993c) Tetrahedron Lett. 34:1261–1264.
Gryaznov and Letsinger (1992).
Helene & Toulme (1990) Biochem. Biophys. Acta, pp. 99–125.
Jablonski et al. (1986) Nucleic Acids Research 14:6115–6128
Kool (1991) J. Am. Chem. Soc. 113:6265–6266.
Lau et al. (1993) Lancet 341:1501–1504
Letsinger & Wu (1994) Amer. Chem. Soc. 116:811–812
Lewis (1986) Adv. Photochem 13:165–235
Lowe (1986) Clinica Chimica Acta, 157:1–32.
Luebke and Dervan (1991). J. Am. Chem. Soc. 113:7447–7448.
Luebke and Dervan (1992) Nucleic Acids Res. 20:3005–3009.
Maniatis, et al. (1982) Molecular Cloning, Cold Springs Harbor Lab., pp.382–389
NAMA Proceedings, International Conference on Nucleic Acid Medical Applications, Cancun, Mexico, Jan. 26–30, 1993, pp. 59–63
Naylor and Gilham (1966) Biochemistry 5:2722–2728.
Peters et al., J. Phys. Chem. 1993, 97:5482–5485.
Prakash and Kool, J. Am. Chem. Soc., 1992, 114:3523–3527.
Purmal et al., Nucleic Acids Res., 1992, 20:3713–3719.
Roberts (1990) J. NIH Res. 2:82–85
Salunkhe et al., J. Am Chem. Soc. 1992, 114:8768–8772.
Shabarova, Biochimie, 1988, 70:1323–1334.
Sokolova et al., FEBS Letters, 1988, 232:153–155.
Twomey and Krawetz (1990) Biotechniques 8(5):478–482
Uhlman & Peyman (1990) Chem. Rev. 90:544–548.
Urdea et al. (1988) Nucleic Acids Res. 16:4937–4956.
Urdea et al. (1989) Clinical Chemistry, 35:1571–1575
van Ness and Chen (1991) Nuc. Acids Res. 19:5143–5151
Vries et al., (1986) "A dot-blot screening procedurea for mutated ras oncogenes using synthetic oligodeoxynucleotides" Gene 50:313–320.
Woolf et al. (1992) Proc. Natl. Acad. Sci. 88:7305–7309.
Zhang et al., (1991) "Single-base mutational analysis of cancer and genetic diseases using membrane bound modified oligonucleotides" Nucleic Acids Research, Vol. 19, No. 14, pp. 3929–3933.

We claim:

1. A method of increasing oligonucleotide selectivity in recognition of nucleic acids by:

(a) reversibly binding a first oligomer to a target oligo- or polynucleotide including base units complementary to base units of the oligonucleotide;

(b) reversibly binding a second oligomer to the target oligo- or polynucleotide including base units complementary to base units of the oligonucleotide adjacent to the first oligomer, and wherein one of the oligomers includes a nucleotide having a first reactive group proximate to a nucleotide of the other oligomer which includes a second reactive group capable of spontaneously forming a covalent bond with the first reactive group; and (c) irreversibly covalently joining the oligomers together through the first and the second reactive groups having been brought in proximity to each other upon binding of the oligonucleotides on the target polynucleotide in the absence of added reagent or enzyme.

2. A method as set forth in claim 1, wherein the first oligomer consists of 7 to 20 nucleotides complementary to the target sequence.

3. A method as set forth in claim 1, wherein the second oligomer consists of 10 to 40 nucleotides complementary to the target sequence.

4. A method as set forth in claim 1, wherein the first reactive group is a 3' or 5' terminal α-haloacylamino group and the second reactive group is a 3' or 5' phosphothioate group, said step (c) being further defined as spontaneously forming a thiophosphorylacetylamino bond through the reactive groups.

5. A method as set forth in claim 1 further including the step capturing the target oligo- or polynucleotide on a solid support.

6. A method as set forth in claim 5, wherein the solid support is further defined as a solid surface that binds the target nucleotide.

7. A method as set forth in claim 5, wherein the solid support is further defined as beads.

8. A method as set forth in claim 5, wherein the solid support is further defined as a membrane.

9. A method as set forth in claim 1 further including the step of labelling the joined oligomer in order to detect hybridization to the target oligo- or polynucleotide.

10. A method as set forth in claim 9, wherein the labelling step is further defined by attaching a labelled oligomer to either of the first or second oligomers.

11. A method as set forth in claim 9, wherein the labelling step is further defined by attaching a label to either of the first or second oligomers before hybridization to the target polynucleotide.

12. A method as set forth in claim 11 wherein the label on the first oligomer is distinguishable from the label on the second oligomer.

13. A method as set forth in claim 1 wherein steps (a), (b), and (c) occur in aqueous solution.

14. A method for hybridizing nucleic acids by:
(a) reversibly binding a first oligomer to a target oligo- or polynucleotide including base units complementary to base units of the oligonucleotide;
(b) reversibly binding a second oligomer to the target oligo- or polynucleotide including base units complementary to base units of the oligonucleotide adjacent to the first oligomer wherein one of the oligomers includes a nucleotide having a first reactive group proximate to a nucleotide of the other oligomer which includes a second reactive group capable of spontaneously forming a covalent bond with the first reactive group;
(c) irreversibly covalently joining the oligomers together through the first and the second reactive groups having been brought in proximity to each other upon binding of the oligonucleotides on the target polynucleotide in the absence of added reagent or enzyme;
(d) dissociating the joined first and second oligomers from the target polynucleotide; and
(e) removing the target polynucleotide.

15. A method as set forth in claim 14, wherein the first oligomer has a relatively low affinity and high selectivity to the target polynucleotide.

16. A method as set forth in claim 14, wherein the second oligomer has high affinity for the target polynucleotide.

17. A method as set forth in claim wherein three or more oligomers are bound contiguously and reversibly on the target polynucleotide.

18. A method as set forth in claim 14, wherein the second oligomer is immobilized on an insoluble support.

19. A method as set forth in claim 14 further including the step of labelling the first oligomer in order to detect or measure the presence of the target polynucleotide.

20. A method as set forth in claim 14, wherein the first oligomer consists of 7 to 20 nucleotides complementary to the target sequence.

21. A method as set forth in claim 14, wherein the second oligomer consists of 10 to 40 nucleotides complementary to the target sequence.

22. A method as set forth in claim wherein the first reactive group is a 3' or 5' terminal α-haloacylamino group and the second reactive group is a 3' or 5' phosphothioate group, said step (c) being further defined as spontaneously forming a thiophosphorylacetylamino bond through the reactive groups.

23. A method as set forth in claim 14 wherein steps (a), (b), (c), (d), and (e) occur in aqueous solution.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

AGCAGATG                                                                                                          8

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

GTGTTGGGAA                                                                          10

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

TTCCCAACAC CATCTGCT                                                 18

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:4:

TTCCCAACAC CACCTGCT                                                 18

( 2 ) INFORMATION FOR SEQ ID NO:5:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:5:

CCTCTATT                                                                                     8

( 2 ) INFORMATION FOR SEQ ID NO:6:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TGTCATCC                                                                                            8

( 2 ) INFORMATION FOR SEQ ID NO:7:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:7:

GGATGACAAA TAGAGG                                                                                   16

( 2 ) INFORMATION FOR SEQ ID NO:8:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:8:

GGATGACAAA TAGTGG                                                                                   16

( 2 ) INFORMATION FOR SEQ ID NO:9:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:9:

GGTTGACAAA TAGAGG                                                                                   16